United States Patent
Schulhauser et al.

(10) Patent No.: US 10,111,643 B2
(45) Date of Patent: Oct. 30, 2018

(54) CARDIAC MONITOR SYSTEM AND METHOD FOR HOME AND TELEMEDICINE APPLICATION

(71) Applicant: Medtronic Vascular, Inc., Santa Rosa, CA (US)

(72) Inventors: Randal Schulhauser, Phoenix, AZ (US); Richard Brown, Mesa, AZ (US); Gerard Bast, Chandler, AZ (US); Dorothy Dominiack, Chandler, AZ (US); William Harding, Chandler, AZ (US); Patrick Kinzie, Glendale, AZ (US); Jeff Cherry, Minneapolis, MN (US); Sneha Saikia, Tempe, AZ (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 133 days.

(21) Appl. No.: 15/072,937

(22) Filed: Mar. 17, 2016

(65) Prior Publication Data
US 2017/0265838 A1    Sep. 21, 2017

(51) Int. Cl.
*A61B 7/04* (2006.01)
*A61B 5/00* (2006.01)
*A61B 5/0456* (2006.01)
*A61B 5/103* (2006.01)

(52) U.S. Cl.
CPC .............. *A61B 7/04* (2013.01); *A61B 5/0456* (2013.01); *A61B 5/103* (2013.01); *A61B 5/746* (2013.01)

(58) Field of Classification Search
CPC ..... A61B 5/0205; A61B 5/746; A61B 5/0456; A61B 5/7275; A61B 5/1116; A61B 5/0245; A61B 5/024; A61B 5/7282
USPC .......................................................... 600/513
See application file for complete search history.

(56) References Cited

U.S. PATENT DOCUMENTS

| | | |
|---|---|---|
| 5,593,431 A | 1/1997 | Sheldon |
| 6,869,404 B2 | 3/2005 | Schulhauser |
| 2004/0167417 A1* | 8/2004 | Schulhauser ........ A61B 5/0006 600/513 |
| 2006/0282000 A1* | 12/2006 | Zhang ................... A61B 5/0031 600/528 |
| 2010/0305633 A1* | 12/2010 | Aziz ..................... A61B 5/0205 607/3 |

OTHER PUBLICATIONS

"Thrombocheck Selfcare Provide You With Safety and Supports Your Well-Being," Brochure, 2pages, CHC CardioHealthCare Gmbh, Oct. 2010.

* cited by examiner

*Primary Examiner* — Niketa Patel
*Assistant Examiner* — Minh Duc Pham
(74) *Attorney, Agent, or Firm* — Medler Ferro Woodhouse & Mills PLLC

(57) ABSTRACT

A system for detecting valvular malfunction includes a monitoring device and a processor. The monitoring device includes a heart sound sensor configured to detect heart sounds of the patient, and a signal processor. The processor is configured to receive a signal representative of the detected heart sounds from the signal processor, wherein the processor is configured to compare the signal to a baseline signal stored in memory. The processor may be part of the monitoring device or may be part of an external device, or both.

20 Claims, 4 Drawing Sheets

CARDIAC MONITOR SYSTEM AND METHOD FOR HOME AND TELEMEDICINE APPLICATION

FIELD OF THE INVENTION

The present invention relates to systems and methods for detecting valvular malfunction in a patient using heart sounds.

BACKGROUND

There are various scenarios in which a patient's heart function should be regularly monitored. In particular, there are various scenarios in which a patient's heart valve function should be regularly monitored. For example, and not by way of limitation, a patient with a known history or a family history of heart valve defects, such as aortic valve stenosis, should be regularly monitored to determine if the heart valve is functioning properly. Further, patients who have had replacement heart valves implanted, regular monitoring is required to determine if the replacement heart valve is functioning properly. Replacement heart valves have a life cycle which is highly variable and unpredictable, depending on various factors such as, but not limited to, patient physiology and personal life style.

The current standard for such regular monitoring is an echocardiogram (also known as "cardiac ultrasound" or "cardiac Doppler"), which determines ejection fraction. However, such testing requires capital equipment and a specialized echocardiogram technician. Therefore, such testing requires the patient to travel to a health care provider to have the test performed. Due to the cost and inconvenience, such testing is performed at periodically, without a means for testing in the time between such visits.

Accordingly, it would be desirable for some patients to have an "in-home" monitoring system to assist in monitoring valvular function between echocardiogram tests or instead of such echocardiogram tests.

SUMMARY OF INVENTION

Embodiments hereof relate to a system for detecting valvular malfunction. The system includes a monitoring device configured to be coupled to a patient. The monitoring device includes a heart sound sensor configured to detect heart sounds of the patient, and a signal processor. The system further includes a processor configured to receive a signal representative of the detected heart sounds from the signal processor, wherein the processor is configured to compare the signal to a baseline signal stored in memory. The processor may be part of the monitoring device or may be part of an external device, or both.

Embodiments hereof also relate to a method for detecting valvular malfunction in a patient. The method includes the steps of sensing heart sound signals, comparing the heart sound signals to baseline heart signals, and alerting the patient if pre-determined metrics of the heart sound signals and the baseline heart signals differ. The method further may include uplinking data corresponding to the heart sound signals to an external device, wherein the comparing step is at the external device. The method may further includes generating a heart sound sensing time period based on electrical signals of the heart, and sensing the heart sound signals with the heart sound sensing time period.

DETAILED DESCRIPTION

Specific embodiments of the present invention are now described with reference to the figures, wherein like reference numbers indicate identical or functionally similar elements. The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

The present description refers to devices and methods for in-home or ambulatory monitoring of valvular function. The devices and methods described herein can be used with a software system that may also be accessible by the patient at home, such as, but not limited to, a portable device application or access to a Telemedicine Network. The devices and methods described herein relate to using heart sounds to determine heart valve performance.

Figure 1:
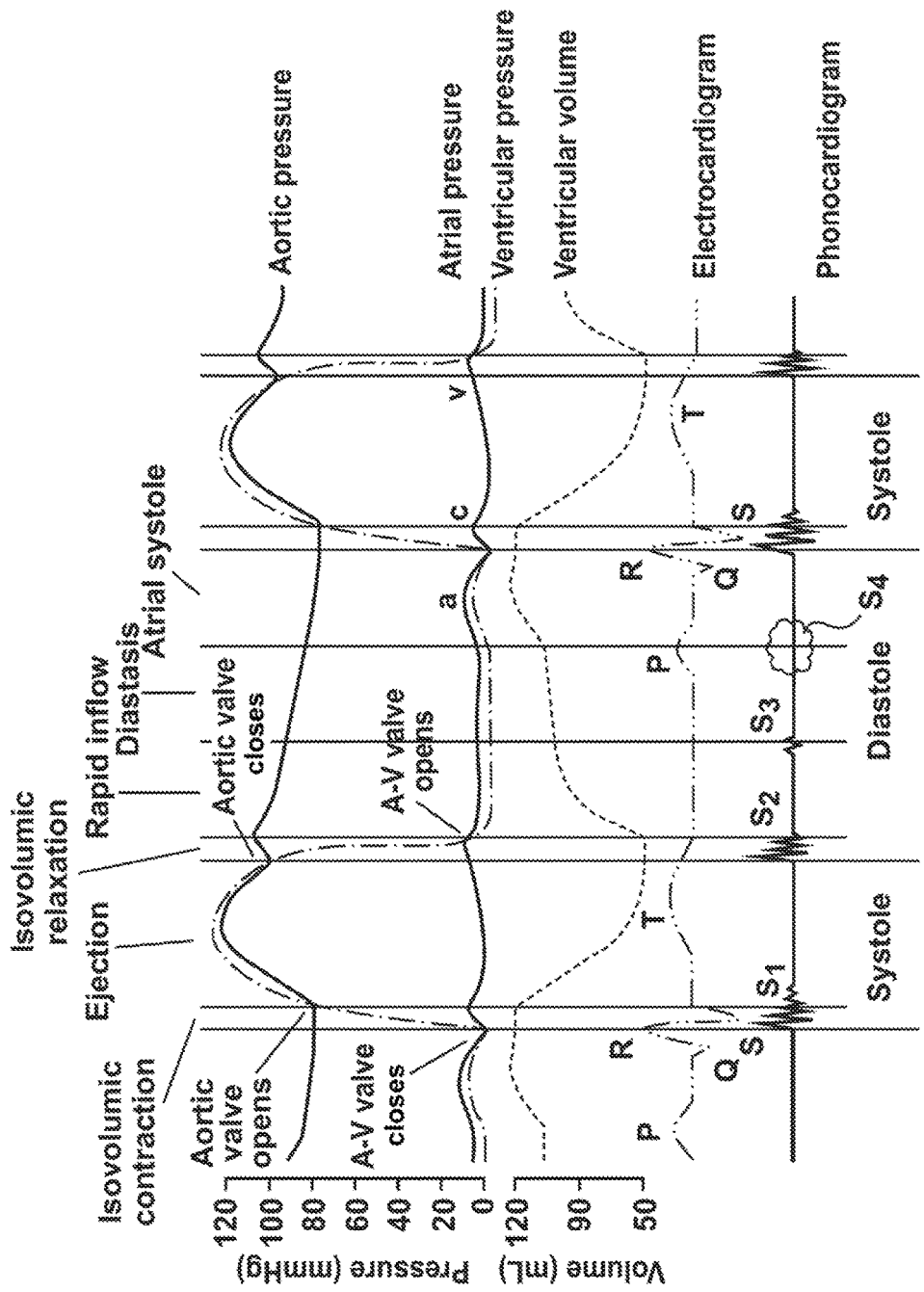
FIG. 1 is "Wiggers" diagram illustrating various parameters of the cardiac cycle plotted against time.

FIG. 1 is a graphical representation of simultaneous ECG events, blood pressure changes and heart sounds that occur in the left ventricle during a cardiac cycle, also known as a "Wiggers diagram". The graphical representation of FIG. 1 will be used to explain the cardiac cycle and the heart sounds associated therewith. Referring to FIG. 1, the stage labeled "diastasis" is when the semilunar valves (the pulmonary valve and the aortic valve) close, the atrioventricular (AV) valves (the mitral valve and the tricuspid valve) open, and the whole heart is relaxed. The stage labeled "atrial systole" is when the atrium contracts, and blood flows from atrium to the ventricle. The stage labeled "isovolumic contraction" is when the ventricles begin to contract, the AV and semilunar valves close, and there is no change in volume. The stage labeled "ejection" is when the ventricles are contracting and emptying, and the semilunar valves are open. During the stage labeled "isovolumic relaxation time", pressure decreases, no blood enters the ventricles, the ventricles stop contracting and begin to relax, and the semilunar valves close due to the pressure of blood in the aorta.

Still referring to FIG. 1, in the atrial pressure plot, the wave "a" corresponds to atrial contraction, the wave "c" corresponds to an increase in pressure from the closed mitral valve bulging into the atrium during ventricular systole, and wave "v" corresponds to passive atrial filling.

In the electrocardiogram plot, the wave "P" corresponds to the onset of atrial depolarization, waves "QRS" (also referred to as "the QRS complex") correspond to the onset of ventricular depolarization, and wave "T" corresponds to ventricular repolarization.

In the phonocardiogram, the first heart sound $S_1$ is caused at least in part by the reverberation of blood from the sudden closure of the mitral valve (left A-V valve). First heart sound $S_1$ generally has a duration of about 150 ms and a frequency on the order of about 10 to 150 Hz. The second heart sound $S_2$ is caused at least in part by the reverberation of blood from the closure of the aortic valve and pulmonary valve. The second heart sound $S_2$ generally has a duration of about 120 ms and a frequency on the order of 50 Hz. The third heart sound $S_3$ is associated with early, passive diastolic filling of the ventricles. The third heart sound $S_3$ is generally difficult to hear in a normal patient using a stethoscope. The fourth heart sound $S_4$ is associated with late, active filling of the ventricles due to atrial contraction. The fourth sound heart sound $S_4$ is generally not heard in a normal patient. Presence of the third and fourth heart sounds during an examination using a stethoscope may indicate a pathological condition. Physicians are particularly familiar with evaluating heart sounds as part of a basic physical examination, and a stethoscope is a standard component in a physician's diagnostic tool box.

The present application relates to devices and methods for in-home monitoring of heart sounds and comparison of the monitored heart sounds to baseline heart sounds to determine if changes in the heart sounds have occurred, and whether such changes warrant further follow-up with a health care professional.

Figure 2:
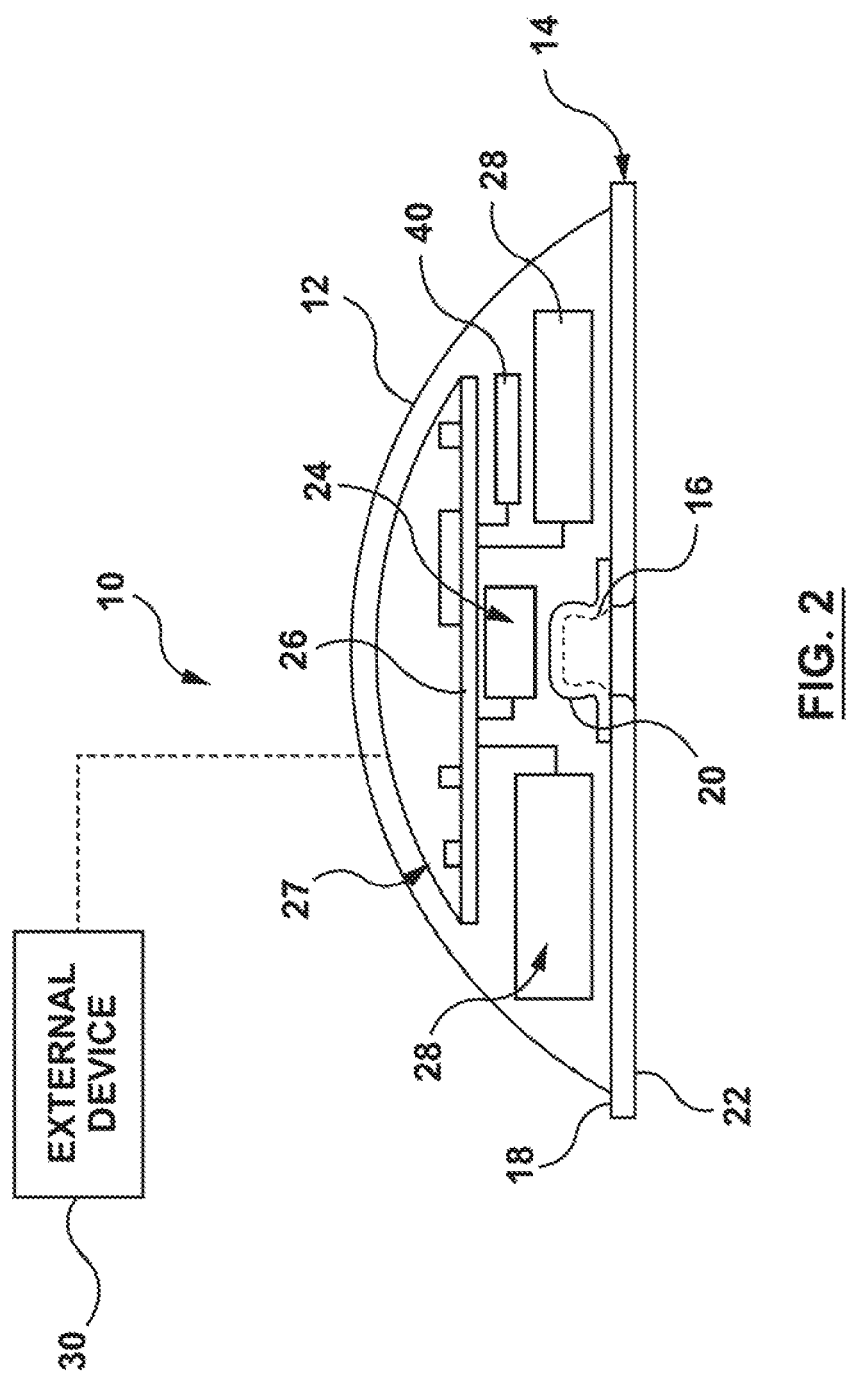
FIG. 2 is schematic view of an embodiment of cardiac monitor and an external device.

FIG. 2 shows schematically an embodiment of a cardiac monitor 10 for monitoring and storing heart sound data according to the present application. In the embodiment shown, cardiac monitor 10 includes a housing 12 configured to be attached to a patch 14. In the embodiment shown, housing 12 is dome shaped. However, housing 12 may be of any shape suitable for the purposes described herein. In the embodiment shown, patch 14 may be a conventional ECG gel electrode patch and includes a snap connector 16 extending from a first surface 18 thereof. Housing 12 includes a recess 20 sized and shaped to connect with snap connector 16. Patch 14 includes a second surface 22 for temporary adherence to the patient. Although a snap connector ECG patch is shown, other ECG patches may be used, or a patch may be formed integrally with housing 12. Further, in some embodiments, the ECG feature may be eliminated such that patch 14 may be simply for temporary adherence to the patient.

Cardiac monitor 10 further includes a heart sound sensor 24. Heart sound sensor 24 may be formed from a piezoelectric material, which may be a piezoelectric ceramic, film, or polymer. Heart sound sensor 24 may be provided as a hard piezoelectric ceramic, a relatively soft piezoelectric ceramic, or a flexible piezoelectric film formed from a piezoelectric polymer such as polyvinylidene fluoride. A soft piezoelectric ceramic such as Model PZT-5A available from Morgan Electro Ceramics, may provide a suitable sensitivity for measuring heart sounds. In an alternative embodiment, heart sound sensor 24 may be provided as a miniaturized microphone. However, an advantage of the piezoelectric material embodiment is that a piezoelectric material does not require an energizing power supply, allowing the battery size required by cardiac monitor 10 to be minimized, reducing the overall size of cardiac monitor 10. Heart sound sensor 24 may be mounted on or within housing 12, and electrically coupled to a circuit board or electronic assembly 26 within housing 12.

Cardiac monitor 10 further includes a power source. In the embodiment shown, the power source is in the form of two batteries 28. However, other suitable power sources may be used. Further, more or fewer batteries 28 may be utilized.

Electronic assembly 26 includes signal processing for processing the ECG signal received from the electrodes of patch 14 and for processing the heart sound signals received from heart sound sensor 24. Electronic assembly 26 may include, for example and not by way of limitation, analog-to-digital converters, filters, amplifiers, memory, spectral analysis, triggers, and other features.

Cardiac monitor 10 further includes an antenna or similar communication device 27 such that cardiac monitor 10 may communicate with an external device 30. External device 30 may be a computer or portable device such as a tablet or mobile phone. External device 30 may include a display such as a computer monitor or a display of a portable device such as a mobile phone or tablet. Further, although electronic assembly 26 is shown as processing the ECG signals and heart sounds signals, some of the processing may be accomplished at external device 30. Accordingly, a computer program product such as a program on a computer or an application ("app") installed on a portable device may perform some or most of the processing described below.

Communication device 27 may be any suitable communication device to transmit and/or receive data to/from external device 30. For example, and not by way of limitation, communication device 27 may be a Bluetooth® wireless communication device, an NFC (Near Field Communication) device, a WiFi device, a wireless USB transmitter, and ultrasonic sound signal, an infrared communication device, or similar device to provide short range data communication from cardiac monitor 10 to external device 30.

Cardiac monitor 10 may further include a position or posture sensor 40, as shown in FIG. 2. The posture of a patient may affect measurements taken by cardiac monitor, such as ECG and heart sounds. Accordingly, it is desirable for the patient to be in the same posture when baseline values and ongoing detected values are measured. Posture sensor 40 may include a plurality of accelerometers, gyros, or magnetometers that generate signals that indicate the posture of a patient. For example, and not by way of limitation, posture sensor 40 may be a 3-axis accelerometer or a gyroscope/accelerometer combination sensor, a plurality of orthogonally aligned accelerometers, or similar sensors for deriving posture. Further information regarding use of orthogonally aligned accelerometers to determine patient posture may be found in a U.S. Pat. No. 5,593,431, which is incorporated by reference herein in its entirety.

A processor of electronic assembly 26, as described below, or a processor in external device 30 may identify postures by comparing the signals generated by posture sensor 40 to one or more respective threshold values. The processor may record in memory the position of the patient when the baseline values are taken. Thereafter, position sensor may prevent usage of cardiac monitor 10 for detection unless the patient is in the same position. Alternatively, cardiac monitor 10 may remind the patient the position for detection and then confirm the position using posture sensor 40.

Figure 3:
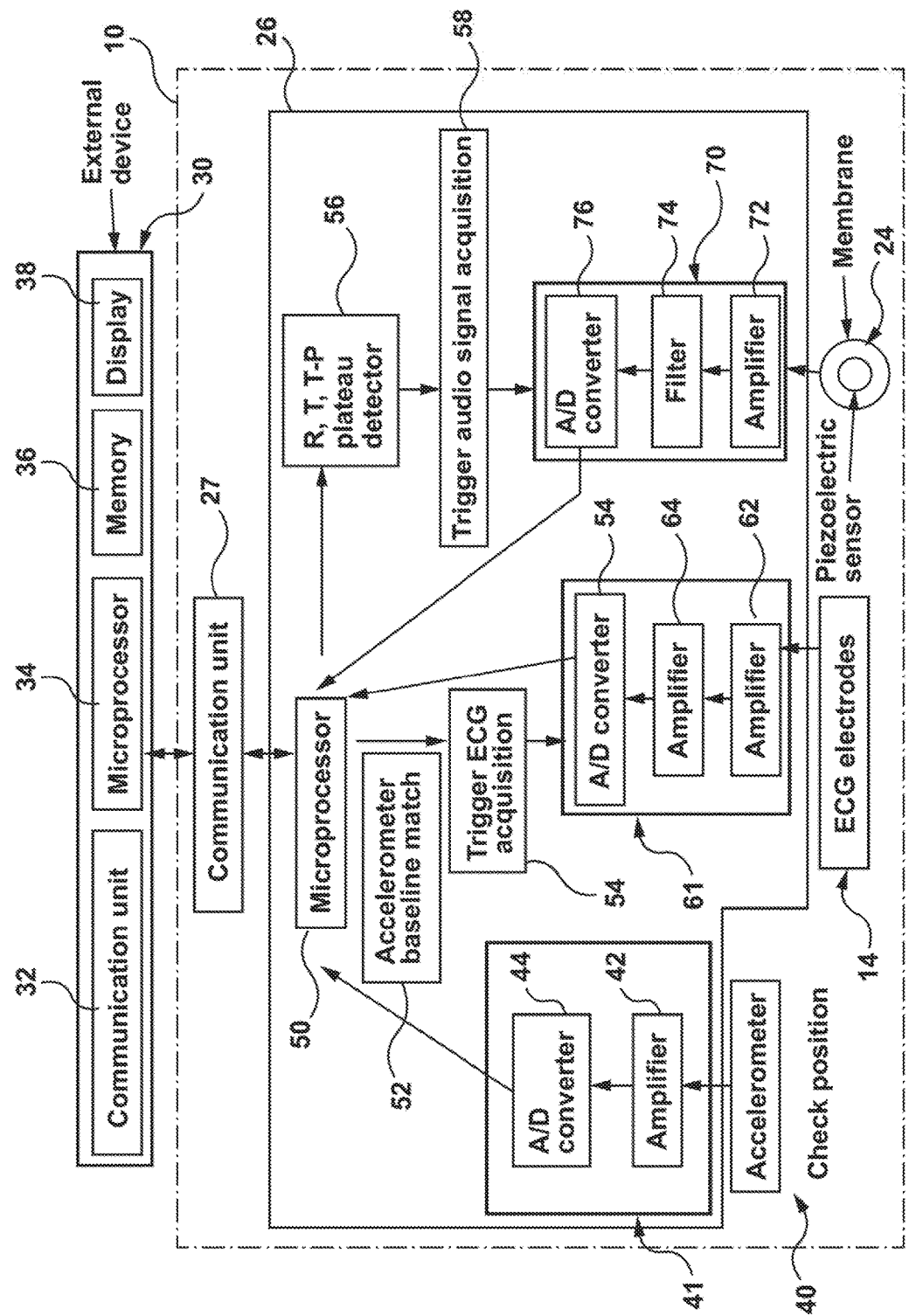
FIG. 3 is a high-level block diagram of a cardiac monitor and external device of FIG. 2.

FIG. 3 shows a high-level block diagram of an exemplary embodiment cardiac monitor 10 and external device 30. As illustrated in FIG. 3, cardiac monitor 10 includes a microprocessor 50 that receives, processes and provides information from/to other systems in cardiac monitor 10. An embodiment of the functions of microprocessor 50 and other systems of cardiac monitor 10 described herein also explains an example of a method of using cardiac monitor 10.

Accordingly, referring to FIG. 3, position sensor 40, which may be an accelerometer as explained above, checks the position of the patient. Position information from position sensor 40 is processed in a position signal processing unit 41. Position signal processing unit 41 may include an amplifier 42 to amplify the signal and analog-to-digital converter 44 to convert the position signal from analog to digital. Other processing device may also be included in signal processing unit 41, as appropriate. This process may be triggered by the patient using the cardiac monitor 10 or using external device 30. Microprocessor 50 checks the position data received from position sensor 40 against a baseline. The baseline for the position data is the position the patient was in when the baseline values, described in more detail below, were measured. When microprocessor 50 has determined that the position data from position sensor 40 matches the baseline position data, as indicated at 52 in FIG. 3, microprocessor triggers ECG acquisition, as indicated at 54.

With ECG acquisition triggered, ECG electrodes, such as in patch 14, bring an ECG signal from the body. The ECG signal processed by an ECG signal processing unit 61. ECG Signal processing unit 61 may include an amplifier 62, a filter 64, and analog-to-digital converter 66. Other signal processing devices may be included in ECG signal processing unit 61, as appropriate. The amplified, filtered, and digitized ECG signal is then processed by microprocessor 50 to trigger audio signal detection, as described below.

Microprocessor 50 uses the ECG signal to detect certain events in the cardiac cycle to trigger heart sound sensor 24 such that signals from heart sound sensor 24 can be received during selected times in the cardiac cycle. For example, and not by way of limitation, microprocessor 50 may include an R-wave, T-wave, and T-P plateau detector 56. R-wave and T-wave sensing known for use in pacemakers and implantable cardioverter defibrillators may be adapted for use in the present invention. Although FIG. 3 shows detector 56 as a single detector, detector 56 may be multiple detectors for detecting desired points in the cardiac sample. Further, while FIG. 3 shows detection of the R-wave, the T-wave, and the T-P plateau, this is just an example, and other points in the cardiac cycle may be used to trigger heard sound sensor 24.

When a desired point in the cardiac cycle is detected by detector 56, microprocessor 50 triggers heart sound sensor 24 and heart sound processing unit 70 to begin audio signal acquisition, as shown at 58 in FIG. 3. For example, and not by way of limitation, heart sound processing unit 70 may be enabled for receiving a signal from heart sound sensor 24 when detector 56 detects the desired point in the cardiac cycle. Heart sound processing unit 70 may be set to receiving a signal from heart sound sensor 24 for a predetermined amount of time after detector 56 has detected an R-wave, a T-wave, and/or a T-P plateau. For example, and not by way of limitation, such a predetermined window may be set by a gain and mode register, or other ways known to those skilled in the art.

With heart sound signal processing unit 70 activated, it receives signals from heart sound sensor 24. Heart sound signal processing unit 70 may include an amplifier 72, a filter 74, and analog-to-digital converter 76. Other signal processing devices may be included in heart sound signal processing unit 70, as appropriate. The amplified, filtered, and digitized heart sound signals are sent to microprocessor 50 for further processing.

In some embodiments, microprocessor 50 sends the heart sound signals from heart sound sensor 24 to external device 30 via communication device 27. As explained above, communication device 27 may be a Bluetooth® wireless communication device, an NFC (Near Field Communication) device, a WiFi device, a wireless USB transmitter, and ultrasonic sound signal, an infrared communication device, or similar device to provide short range data communication from cardiac monitor 10 to external device 30. Communication device 27 includes an antenna and/or other transceiver device or circuitry to communicate with external device 30.

In an embodiment, external device 30 includes a communication unit 32, a microprocessor 34, memory 36, and a display 38. External device 30 may include other features and devices related or unrelated to the present disclosure. As explained above, external device 30 may be a computer or portable device such as a tablet or mobile phone. Display 38 may be a computer monitor or a display of a portable device such as a mobile phone or tablet. Microprocessor 34 and memory 36 are used to compare heart sound signals to baseline data, as explained in more detail below. As also explained below, microprocessor 50 of cardiac monitor 10 may perform some or all of the functions described below with respect to comparison. Further, electronic assembly 26 of cardiac monitor 10 may include memory (not shown) to perform some or all of the memory functions described below.

Figure 4:
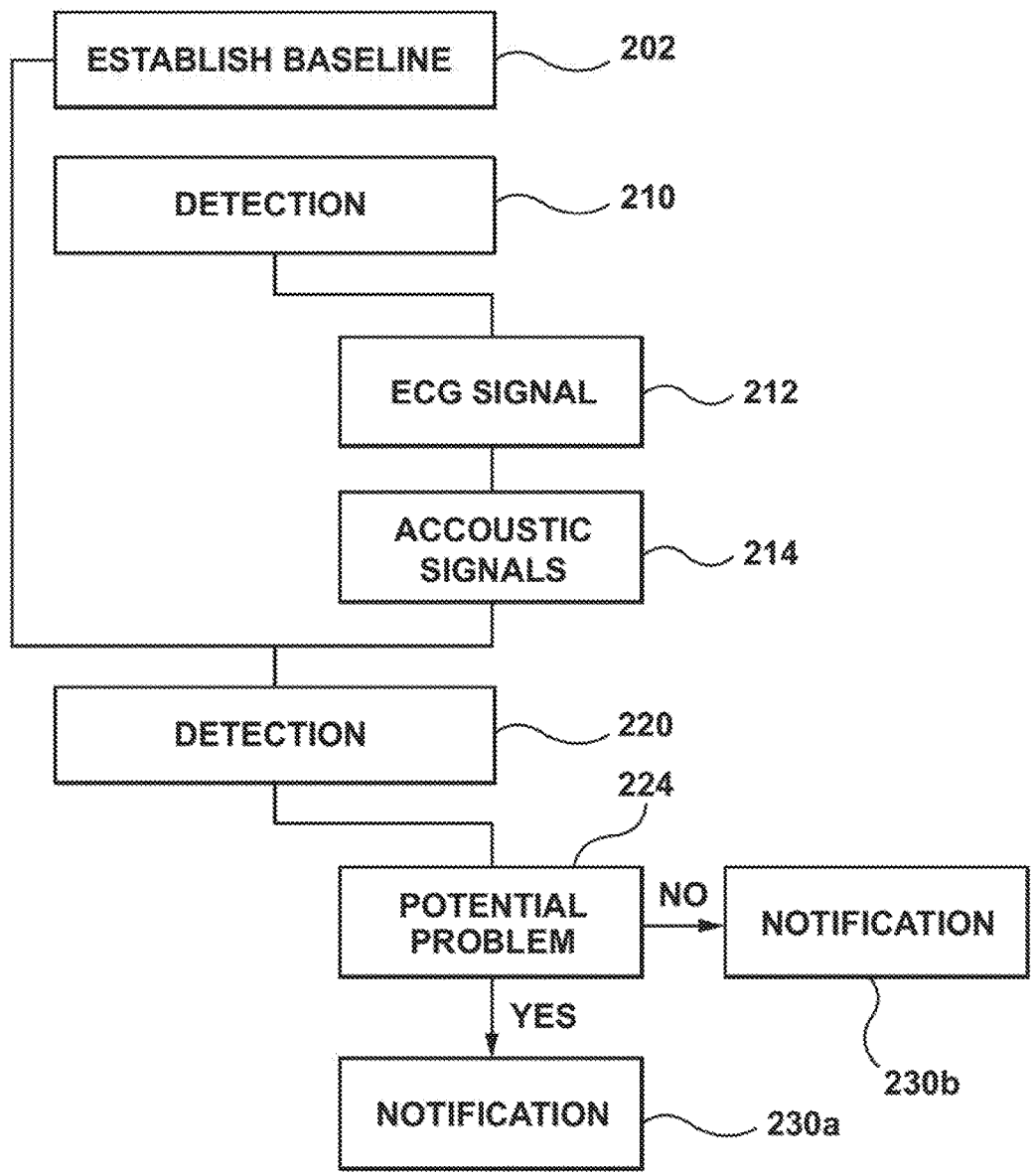
FIG. 4 is a flow chart providing an overview of an embodiment of a method for monitoring a patient's valvular function utilizing heart sounds.

FIG. 4 is a flow chart providing an overview of an embodiment of a method 200 detecting valvular stenosis or other valvular malfunctions. Method 200 may be used to detect valvular malfunctions in a native valve or prosthetic tissue valve. In step 202 of the method 200, baseline values of key metrics are established. The baseline values of key metrics may be established using the devices described herein. Further, the baseline values may be established with the specific cardiac monitor 10 described above. In such a manner, differences between the baseline values and the tested values, described below, are less likely to be due to changes in the cardiac monitor. The baseline values may be established in conjunction with an examination at a physician's office, hospital, or other medical care facility such that it can be confirmed that the baseline values are established while the valve or prosthetic valve is functioning normally.

The key metrics that may be measured and stored as the baseline values may include the first heart sound spectral power, the second heart sound spectral power, the third heart sound spectral power, and/or the fourth heart sound spectral power.

In some embodiments, a key metric to be measured and stored may include peak detection in spectral analysis. For example, and not by way of limitation, the first heart sound S1 normally is in the frequency range of approximately 10 Hz to 150 Hz, the second heart sound S2 is normally in the range of approximately 10 Hz to 400 Hz, and the third heart sound S3 is normally in the range of approximately 10 Hz to 60 Hz. When storing baseline values, these heart sounds are measured by cardiac monitor 10 and the measured values are stored in memory. Thus, when measured later by cardiac monitor 10, the values may be compared. In this example, the peak frequency of the power spectrum for each heart sound should lie within the ranges noted above.

In some embodiments, a key metric to be measured and stored may include ejection fraction. Ejection fraction is the time interval from electric stimulation (R-wave in the ECG) to opening of the aortic valve divided by the time interval from opening of the aortic valve to closing of the aortic valve. A "normal" ejection fraction is 50% to 75%. Therefore, ejection fraction may be measured when establishing baseline values and stored in memory for later comparison.

In some embodiments, a key metric to be measured and stored is a ratio of the S2-S1 time interval to the S1-S2 time interval. The S2-S1 time interval is normally longer than the S1-S2 time interval (i.e., ratio above 1). For example, and not by way of limitation, the S2-S1 time interval may be up to twice as long as the S1-S2 time interval (ratio of 2:1). This ratio may be measured when establishing baseline values and stored in memory for later comparison.

In some embodiments, a key metric to be measured and stored includes heart beat cycle period. A "normal" heart beat cycle period is in the range of 0.8 second, 0.3 second systole, and 0.5 second diastole. The heart beat cycle can be measured when establishing baseline values and store in memory for later comparison.

Referring back to FIG. 4, the baseline values established in step 202 may be stored in memory, for example, memory 36 of external device 30 (FIG. 3). As explained above, alternatively, memory may be housed in cardiac monitor 10.

Step 210 of the method is a detection step using cardiac monitor 10, as shown in FIG. 4. Step 210 may be an at-home detection step. In an embodiment, cardiac monitor 10 includes ECG detection 212 and heart sound detection 214. The ECG detection 212 may be used to trigger the heart sound detection 214, as explained above with respect to FIG. 3. For example, and not by way of limitation, the detection of the R-wave by the ECG detection may trigger receiving of heart sound signals using sound sensor 24 to record the first heart sound S1, as explained above. Similarly, detection of the T-wave may trigger recordation of the second heart sound S2, detection of the T-P wave plateau may trigger recordation of the third heart sound S3, and a time delay off of detection of the T-P wave plateau may trigger recordation of the fourth heart sound S4 (if it exists).

The detection step 210 may take place over a range of cardiac cycles. For example, and not by way of limitation, a detection period for detection step 210 may occur for 10 seconds as a patient holds their breadth. Depending on the patient's heart rate, a range of cardiac cycles in the range of 5 to 20 cardiac cycles may be detected during this time period. With patients with slower heart rates, a longer time period may be desirable for the detection step 210. Thus, in some embodiments a detection period the detection step 210 may be in the range of 5-20 seconds. Further, it may be desirable to perform several detection periods within detection step 210. For example, and not by way of limitation, it may be desirable to perform 2-5 successive recordings of 10-15 seconds each.

After the detection step 210, the acoustic signals from the detection step 210 are compared to the saved baseline metrics in comparison step 220. Comparison step 220 includes processes such that the acoustic signals and baseline signals are in proper format for comparison, such as signal processing steps including filtering, compression, analog-to-digital conversion, and other processes, as appropriate. As explained above, the comparison step may be performed by microprocessor 50 of cardiac detection device 10 or microprocessor 34 of external device 30. In some embodiments, as noted above, a baseline metric of peak frequency of heart sounds S1, S2, and S3 may be established during step 202. During the detection step, the heart sounds S1, S2, and S3 are recorded. In some embodiments, during comparison step 220, a high resolution sweep from 10 Hz to 400 Hz may be performed to search for extra peaks or shifts in peak frequency of the power spectrum as compare to the baseline.

Murmurs may have a frequency of up to 1000 Hz. In some embodiments, a lower resolution sweep from 200 Hz to 1000 Hz may be performed to search for new peaks as compared to the baseline.

In step 224, the microprocessor 36 or 50 determines whether the comparison between the measured data and the baseline values reveals a potential problem with the valvular function. This step may be accomplished by establishing a pre-set acceptable variation from the baseline values. If the measured data is outside of the pre-set acceptable variation from the baseline values, then there may be a problem with the valvular function.

As explained above, for example, and not by way of limitation, part of step 224 may be to compare measured peak frequency of heart sounds S1, S2, and S3 compared to baseline peak frequencies. If a measured peak frequency varies by more than a predetermined percentage of a corresponding baseline peak frequency, then the measured heart sound is outside of the pre-set acceptable variation. For example, and not by way of limitation, this predetermined percentage may vary depending on the baseline values and when the baseline values are established (e.g., before surgery, shortly after surgery, or several years after surgery). In another non-limiting example, if the measured ejection fraction is outside of the normal range of 50% to 75%, step 224 reveals a potential problem.

Referring back to FIG. 4, if the comparison in step 224 reveals a potential problem, a notification step 230a of the method alerts the patient to see a healthcare professional on a display. This alert can be in various forms. For example, and not by way of limitation, an alarm may appear (sound and/or message) on a mobile device of the patient. For example, and not by way of limitation, if the software is implemented in the form of a mobile application, the application will provide an alarm on the mobile device. If the software is implemented via a telemedicine network over an internet connection, an alarm may appear on the computer, may be sent to the patient via text or e-mail, and/or may be sent directly to the patient's healthcare provider. Those skilled in the art would recognize that other types of alerts may be utilized.

On the other hand, if step 224 reveals that there is not a potential problem based on the comparison, a notification step 230b of the method alerts the patient that a problem was not discovered. This alert may be in various forms, as described above. Further, as part of the alert, an appointment for the next testing date may be sent to the user.

Method 200 may be executed continuously by repeating steps 210-224 for a predetermined number of cardiac cycles such that ECG and heart sound data are stored on a beat-by-beat basis in temporary looping memory buffers. At any time, a manual or automatic trigger causes cardiac monitor to save a predetermined interval of ECG and heart sound data in long-term memory.

Increased time resolution of heart sound data may be desired for more precise estimation of blood pressure. Therefore in one embodiment, a higher sampling rate may be selected, for example on the order of 1 KHz. In order to store the same duration of data acquired at the higher sampling rate, the memory capacity would need to be increased accordingly. In addition, battery current drain would be increased by the higher sampling rate, shortening the device longevity or requiring a larger battery, increasing overall device size.

In some embodiments, calibration steps may be desirable for accuracy of results. For example, and not by way of limitation, if cardiac monitor 10 is used to monitor a patient that has had valve replacement surgery, baseline metrics may be recorded after surgery. A subsequent reading can be taken immediately after the baseline has been stored for comparison to "self-calibrate" the cardiac monitor. In another non-limiting example, after notification to see a physician due to a potential problem, the device may be re-calibrated to establish a new baseline and may be adjusted to provide tighter tolerances in the comparison step.

In another non-limiting example, cardiac monitor 10 may be used for convenient general purpose screening. In such a case, cardiac monitor 10 and the microprocessor (whether part of cardiac monitor 10 or external device 30) may be calibrated to compare the measured signals to "normal" signals for the type of patient being screened. For example, and not by way of limitation, if the population being screened is the general population in a certain age group, the "normal" baseline values for such screening may be adjusted to the "normal" baseline values for such an age group. In another non-limiting example, if the group being screened is a group which has undergone heart valve replacements, the "normal" baseline values may be adjusted to what is considered "normal" for patients who have undergone heart valve replacement surgery (e.g. research has shown that following surgery there is a shift in the frequency spectrum).

While only some embodiments and methods have been described herein, it should be understood that it has been presented by way of illustration and example only, and not limitation. Various changes in form and detail can be made therein without departing from the spirit and scope of the invention, and each feature of each embodiment discussed herein, and of each reference cited herein, can be used in combination with the features of any other embodiment. All patents and publications discussed herein are incorporated by reference herein in their entirety.

What is claimed is:

1. A system for detecting aortic stenosis comprising:
   a monitoring device configured to be coupled to a patient, the monitoring device including a heart sound sensor configured to detect heart sounds of the patient, and a signal processor; and
   a processor configured to
      receive a signal representative of the detected heart sounds from the signal processor and process the signal representative of detected heart sounds to determine tested values of at least one of,
         peak frequencies of a first heart sound, a second heart sound, and a third heart sound of the patient, wherein the first heart sound is detected at closure of a mitral valve of the patient, the second heart sound is detected at the closure of an aortic valve and a pulmonary valve of the patient, and the third heart sound is detected at passive diastolic filling of ventricles of the patient,
         a ratio of a first time period from the second heart sound in a first cardiac cycle to the first heart sound in a second cardiac cycle and a second time period from the first heart sound in the second cardiac cycle to the second heart sound in the second cardiac cycle, and
         a heart beat cycle period including a systole period and a diastole period, and
      compare at least one of the tested values to corresponding baseline values of the peak frequencies, the ratio, and the heart beat cycle periods stored in memory.

2. The system of claim 1, further comprising an alert coupled to the processor, wherein the processor is configured to activate the alert if the at least one of the tested values deviates from the corresponding baseline value in a predetermined manner.

3. The system of claim 2, wherein the alert is an audio alert.

4. The system of claim 2, wherein the alert is a display in communication with the processor.

5. The system of claim 1, further comprising a second sensor configured to sense electrical activity of the patient's heart, wherein the processor is configured to receive electrical activity signals from the second sensor.

6. The system of claim 5, further comprising an event trigger device transmitting a trigger signal to the monitoring device and the processor, wherein the processor is further configured to generate a first heart sound sensing time period and a second heart sound sensing time period, and wherein the heart sound sensor is configured to detect the first heart sound within the first heart sound sensing time period and the second heart sound within the second heart sound sensing time period, and wherein the processor is configured to store data corresponding to the first heart sound and the second heart sound in response to the trigger signal.

7. The system of claim 6, wherein the first heart sound sensing time period is configured to commence in response to the second sensor sensing an R-wave in the electrical activity of the patient's heart.

8. The system of claim 7, wherein the second heart sound sensing time is configured to commence in response to the second sensor sensing a T-wave in the electrical activity of the patient's heart.

9. The system of claim 1, wherein the monitoring device further includes a posture sensor.

10. The system of claim 9, wherein the posture sensor includes an accelerometer, wherein the posture sensor is configured to communicate with the processor to ensure that the patient is in a desired position.

11. The system of claim 1, wherein the processor is determine the tested values of each of the peak frequencies, the ratio, and the heart beat cycle periods, and
    wherein the processor is configured to compare the tested values of each of the peak frequencies, the ratio, and the heart beat cycle periods to the corresponding baseline values of the peak frequencies, the ratio, and the heart beat cycle periods.

12. The system of claim 1,
    wherein the monitoring device further includes a second sensor configured to sense electrical activity of the patient's heart,
    wherein the processor is further configured to
       receive electrical activity signals from the second sensor,
       detect an R-wave in the patient's heart cycle,
       measure a first time period from the detection of the R-wave to an end of the first heart sound,
       measure a second time period from the end of the first heart sound to a start of the second heart sound,
       calculate a tested ejection fraction by dividing the first time period by the second time period, and
       compare the tested ejection fraction to a baseline ejection fraction.

13. A method for detecting valvular malfunction in a patient comprising the steps of:
    utilizing a cardiac monitor for in-home sensing of the patient's heart sounds;
    processing the sensed heart sounds to determine tested values of at least one of,
       peak frequencies of a first heart sound, a second heart sound, and a third heart sound of the patient, wherein the first heart sound is detected at closure of a mitral valve of the patient, the second heart sound is detected at the closure of an aortic valve and a pulmonary valve of the patient, and the third heart sound is detected at passive diastolic filling of ventricles of the patient,
       a ratio of a first time period from the second heart sound in a first cardiac cycle to the first heart sound in a second cardiac cycle and a second time period from the first heart sound in the second cardiac cycle to the second heart sound in the second cardiac cycle, and a heart beat cycle period including a systole period and a diastole period, comparing at least one of the tested values the heart sound signals to corresponding baseline values of the peak frequencies, the ratio, and the heart beat cycle periods; and alerting the patient if at least one the tested values deviates from the corresponding baseline value in a pre-determined manner.

14. The method of claim 13, further comprising uplinking data corresponding to the heart sound signals to an external device, wherein the comparing step is at the external device.

15. The method of claim 13, further comprising the steps of:
   detecting an R-wave and a T-wave in the patient's heart using a second sensor;
   starting a first heart sound sensing time period in response to detecting the R-wave, wherein the first heart sound is sensed within the first heart sound sensing time period;
   starting a second heart sound sensing time period in response to detecting the T-wave, wherein the second heart sound is sensed within the second heart sound sensing time period.

16. The method of claim 13, further comprising the step of sensing a position of the patient such that the position of the patient is the same during the step of sensing heart sound signals and when the baseline heart sound signals were measured.

17. The method of claim 13, wherein the step of processing the sensed heart sound signals includes determining the tested values of each of the peak frequencies, the ratio, and the heart beat cycle periods is determined, and
   wherein the comparing step includes comparing the tested values of each of the peak frequencies, the ratio, and the heart beat cycle periods to the corresponding baseline values of the peak frequencies, the ratio, and the heart beat cycle periods.

18. The method of claim 13, further comprising the steps of:
   detecting an R-wave in the patient's heart cycle using a second sensor;
   measuring a first time period from the detection of the R-wave to an end of the first heart sound;
   measuring a second time period from the end of the first heart sound to a start of the second heart sound;
   calculating a tested ejection fraction by dividing the first time period by the second time period; and
   comparing the tested ejection fraction to a baseline ejection fraction.

19. The method of claim 13, wherein the corresponding baseline values are normal values for persons in a same category as the patient.

20. The method of claim 13, wherein the corresponding baseline values are values previously measured from the patient.

* * * * *